(12) United States Patent
Moon et al.

(10) Patent No.: US 6,423,846 B1
(45) Date of Patent: Jul. 23, 2002

(54) HIGH-YIELD METHOD FOR PREPARING LANSOPRAZOLE

(75) Inventors: Young-Ho Moon, Suwon-si; Kyung-Ik Lee, Anyang-si; Gwan-Sun Lee, Seoul, all of (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 09/967,581

(22) Filed: Sep. 28, 2001

(51) Int. Cl.⁷ .............................................. C07D 401/12
(52) U.S. Cl. ...................................... 546/273.7
(58) Field of Search ....................... 546/273.7

(56) References Cited

PUBLICATIONS

CA 108:131818, Nohara et al. 1988.*
CA108:62483, Makino et al., 1988.*

\* cited by examiner

Primary Examiner—Jane Fan
(74) Attorney, Agent, or Firm—Anderson Kill & Olick, PC

(57) ABSTRACT

Lansoprazole of formula (I) can be produced economically in a high yield using a simple, two-step method comprising reacting hydroxymethylpyridine and benzimidazole starting materials in the presence of a phosphine compound and a dialkyl azodicaboxlate and oxidizing the product of the first step in the presence of an organic radical catalyst:

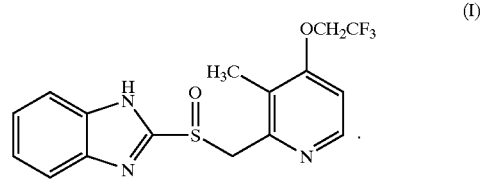

7 Claims, No Drawings

HIGH-YIELD METHOD FOR PREPARING LANSOPRAZOLE

FIELD OF THE INVENTION

The present invention relates to an improved method for preparing lansoprazole, which is simple and gives a high yield.

DESCRIPTION OF THE PRIOR ART

Lansoprazole (2-[3-methyl-4-(2,2,2-trifluoroethoxy)-2-pyridyl]methylsulphinyl-1H-benzimidazole) is effective in preventing the secretion of gastric acid, and therefore, used for treating gastric ulcer, duodenal ulcer and gastritis.

The process for preparing lansoprazole disclosed in U.S. Pat. No. 4,628,098 and Korean Patent No. 52,837 is represented by Scheme 1, wherein the hydroxymethylpyridine derivative of formula (III) is reacted with thionyl chloride to form the chloromethylpyridine derivative of formula (IV), which is reacted with the benzimidazole derivative of formula (V) to form the compound of formula (II), and the compound of formula (II) is oxidized to produce lansoprazole:

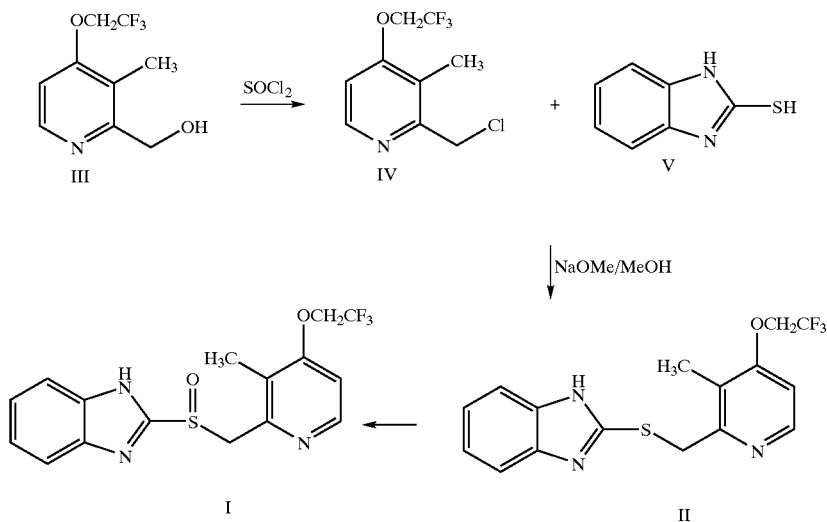

Scheme 1

In this process, however, the compound of formula (IV) formed as an intermediate is highly unstable and gives many byproducts during the reaction with the compound of formula (V), resulting in a low yield of the compound of formula (II).

Further, the oxidation procedures employed in the prior art methods for converting the compound of formula (II) into lansoprazole have problems in that many byproducts are formed and the yield of lansoprazole is low. For example, in EP Patent No. 134,400 and GB Patent No. 2,134,523 as well as U.S. Pat. No. 4,628,098 and Korean Patent No. 52,837, m-chloroperbenzoic acid is used as an oxidant, while Spain Patent Nos. 550,057, 540,147 and 539,793 disclose sodium periodate, iodosomethylbenzene and iodosobenzene, respectively, as the oxidant employed. However, the use of these expensive oxidants results in the production of many impurities and a low yield of the product in the range of about 60 to 80%.

Korean Patent No. 100,796 discloses a high yield method for preparing lansoprazole which involves oxidation of the compound of formula (II) with hydrogen peroxide in the presence of a vanadium compound. However, the use of these expensive oxidants is not viable in the mass production of lansoprazole.

SUMMARY OF THE INVENTION

Accordingly, it is a primary object of the present invention to provide an improved method for the preparation of lansoprazole in a high yield, which can be advantageously used in economic production of lansoprazole.

In accordance with the present invention, there is provided a process for preparing lansoprazole of formula (I) comprising (a) reacting the compound of formula (III) with the compound of formula (V) in the presence of a phosphine compound and an azodicarboxylate to form the compound of formula (II); and (b) reacting the compound of formula (II) with an oxidant in a mixture of water and an organic solvent in the presence of both an organic free radical and a phase transfer catalyst:

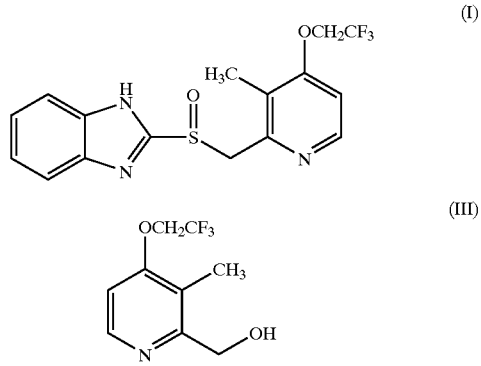

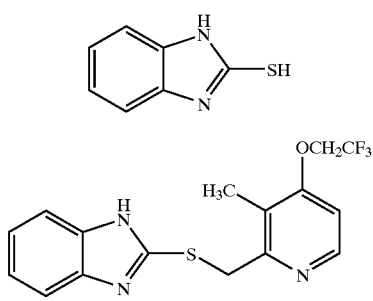

(V)

(II)

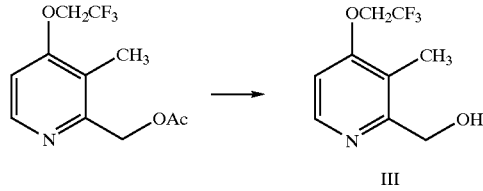

DETAILED DESCRIPTION OF THE INVENTION

The inventive method for preparing lansoprazole of formula (I) may be represented by Scheme 2:

Scheme 2

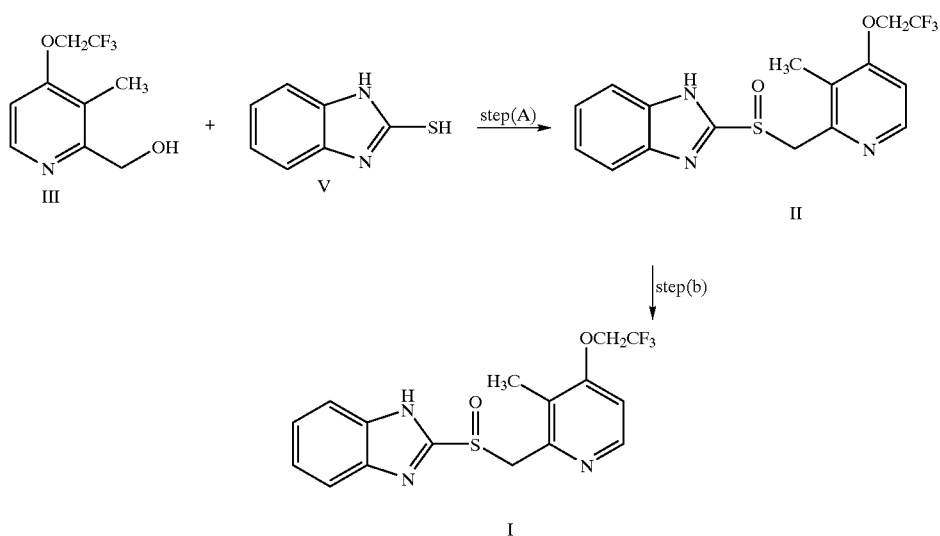

The hydroxymethylpyridine derivative of formula (III) used a starting material in Scheme 2 maybe prepared in accordance with one of the two methods disclosed in U.S. Pat. No. 4,698,333, which are shown in Scheme 3(a) and 3(b):

Scheme 3(a)

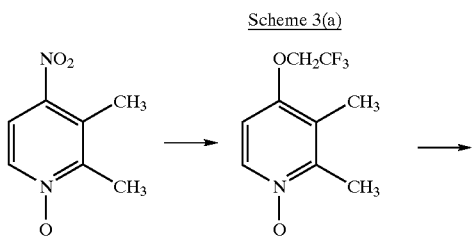

Scheme 3(b)

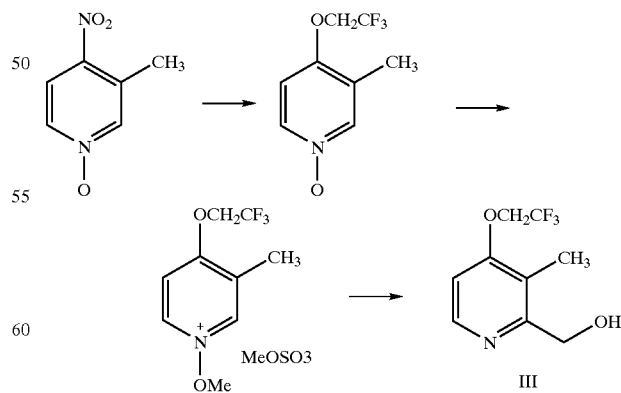

In Step (a) of Scheme 2, the compound of formula (II) is prepared by reacting the compound of formula (III) with the benzimidazole derivative of formula (V) in the presence of a phosphine compound and an azodicarboxylate. This step is much simpler than the two-step procedure employed in the conventional method for preparing the compound of formula (II) (see Scheme 1).

Step (a) of the present invention may be conducted by dissolving a mixture of the compounds of formula (III) and (V) together with aphosphine compound in an appropriate solvent, adding a dialkyl azodicarboxylate thereto, and allowing the reaction to proceed for 1 to 2 hours at 0 to 25° C., wherein the benzimidazole derivative of formula (V) may be used in a 1 to 1.2 equimolar amount based on the hydroxymethylpyridine derivative. This procedure gives a high yield, 95% or higher, of the compound of formula (II).

The reaction pathway involved in Step (a) is shown in Scheme 4, wherein triphenylphosphine($Ph_3P$) represents the phosphine compound:

or diethyl azodicarboxylate(DEAD). The dialkyl azodicarboxylic acid may be used in a 1 to 1.5 equivalent amount, preferably, 1.1 equivalent amount, based on the compound of formula (III).

The compound of formula (II) prepared in Step (a) can be recovered in the form of a crystal, which can be isolated by simple filtration, and there is no need to employ the complicated column chromatography purification procedure used in the conventional method.

In Step (b) of Scheme 2, lansoprazole is prepared by oxidizing the compound of formula (II) produced in Step (a) in the presence of both a free radical catalyst and a phase transfer catalyst, in a mixture of water and an organic solvent.

For example, the procedure of Step (b) may involve oxidizing the compound of formula (II) with an oxidant e.g.,

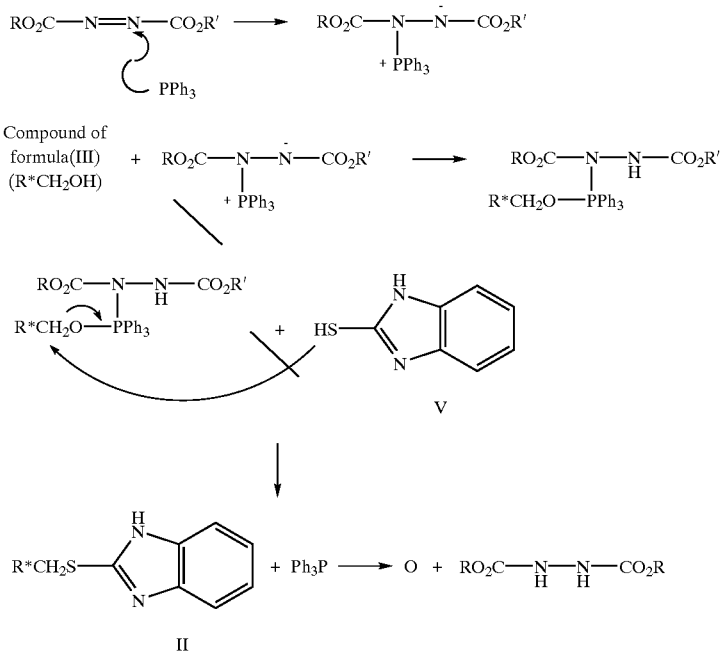

wherein: R and R' are each independently a $C_{1-5}$ alkyl group and R* is 3-methyl-4-(2,2,2-trifluoroethoxy)-2-pyridyl.

The organic solvent used in Step (a) of the present invention may be selected from the group consisting of chloroalkanes, e.g., dichloromethane, chloroform and 1,2-dichloroethane; aromatic hydrocarbons, e.g., benzene, toluene and xylene; ethers, e.g., tetrahydrofuran, diisopropylether, methyl t-butylether and dioxane; ketones, e.g., methylisobutylketone; nitriles, e.g., acetonitrile; amides, e.g., dimethylacetamide and dimethylformamide; and a mixture thereof.

The phosphine compound which can be used in the present invention includes triethylphosphine, trimethylphosphine, tributylphosphine and triphenylphosphine, among which triphenylphosphine is preferred. The phosphine compound may be used in a 1 to 1.5 molar amount, preferably, 1.1 mole, based on a mole of the compound of formula (III).

Further, the dialkyl azodicarboxylate which can be used in the present invention includes diisopropyl azodicarboxylate sodium hypochlorite (NaOCl), in a mixture of water and an organic solvent in the presence of both a phase transfer catalyst and an organic free radical at 0 to 20° C. for 2 to 4 hours, to obtain lansoprazole in a high yield of 90% or higher.

Thus, Step (b) of the present invention is characterized by its high yield, which is due to the fact that the formation of byproduct impurities is almost completely suppressed. For example, such a byproduct as the compound of formula (VI) is produced in a large amount when a conventional method is used or when any of the above-mentioned two catalysts is not used, but only to the extent of 0.1% when the inventive procedure is employed:

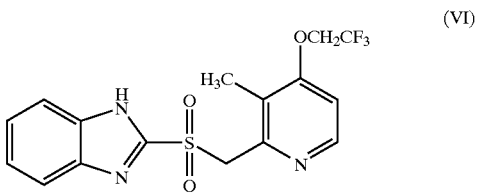

(VI)

The organic radical catalyst which may be used in the present invention includes diphenyl nitrosyl radical, di-tert-alkyl nitrosyl radical, 2,2,6,6-tetramethyl-1-pyperidinyloxy (TEMPO) free radical and 4-methoxy-TEMPO free radical. The organic radical catalyst may be used in a catalytic amount, 1 mole% or less based on the amount of the compound of formula (II).

The oxidant is used in a 1 to 3 equivalent amount, preferably a 2.2 equivalent amount, based on the compound of formula (II) and it may be sodium hypochlorite.

The oxidation of step (b) is carried out in a two-phase system, i.e., in a mixture of water and an organic solvent, in the presence of a phase transfer catalyst. The organic solvent used in Step (a) may also be used in Step (b) and mixed with water in an appropriate ratio, preferably 1:1 to 2:1.

The phase transfer catalyst which may be used in Step (b) includes tetrabutyl ammonium fluoride, tetrabutyl ammonium chloride, tetrabutyl ammonium bromide and tetrabutyl ammonium iodide.

The final product may be separated from the organic phase by dissolving in an aqueous acid solution, neutralizing the solution to crystallize lansoprazole, and filtering.

As described above, according to the simple, two-step method of the present invention, lansoprazole can be obtained in a high yield.

While the invention has been described with respect to the specific embodiments, it should be recognized that various modifications and changes may be made by those skilled in the art to the invention which also fall within the scope of the invention as defined by the appended claims.

EXAMPLE

Example 1

Preparation of 2-[3-methyl-4-(2,2,2-trifluoro ethoxy)-2-pyridyl]methylthio-1H-benzimidazole(the compound of formula (II)) (Step (a))

A mixture of 6.63 g of 2-hydroxymethyl-3-methyl-4-(2,2,2-trifluoroethoxy)pyridine(30 mmol), 4.5 g of 2-mercaptobenzimidazol(30 mmol) and 8.67 g of triphenyl phosphine(33 mmol) was dissolved in 100 ml of tetrahydrofuran, 5.75 g of diethyl azodicarboxylate(DEAD) (33 mmol) dissolved in 30 ml of tetrahydrofuran was added dropwise thereto at room temperature, and stirred for 1 hour. The reaction mixture was concentrated under a reduced pressure, the resulting residue was combined with looml of ethylacetate, and extracted twice with 50 ml portions of 1N—HCl. The aqueous layer was then washed with 50 ml of diethylether; neutralized with 1N—NaOH to adjust the pH to 7. The resulting precipitates were filtrated, washed with water, and dried, to obtain 10.06 g of the title compound as a white solid(yield: 95%).

m.p.: 142–144° C.

Mass: m/z=354.1(M+1)$^+$, 321.1, 235.9, 119.0

H-NMR(300 MHz, CDCl$_3$) δ (ppm): 2.33(s,3H), 4.40–4.47(q,2H), 4.44(s,2H), 6.72–6.74(d,1H), 7.17–7.20 (m,2H), 7.53–7.56(m,2H), 8.41–8.43(d,1H)

Example 2

Preparation of 2-[3-methyl-4-(2,2,2-trifluoro ethoxy)-2-pyridyl]methylsulphinyl-1H-benzimidazol (the compound of formula(I))(lansoprazole) (Step (b))

4.46 g of 2-[3-methyl-4-(2,2,2-trifluoroethoxy)-2-pyridyl]methylthio-1H-benzimidazole(12 mmol) prepared in Example 1 and 18.74 mg of tetramethyl-1-piperidinyloxy (TEMPO) free radical (1 mol %, used as a catalyst) were dissolved in 40 ml of tetrahydrofuran, and combined with 166.76 mg of tetrabutyl ammonium chloride (5 mol %) dissolved in 20 ml of distilled water. The resulting mixture was cooled to 0° C. and 13.6 ml of NaOCl (12%, 2.2 equivalent) dissolved in 20 ml of distilled water was added thereto over 2 hours at 0° C., stirred for 10 minutes at 0° C., and then for additional 10 minutes at 20° C. Then, the reaction mixture was extracted with 40 ml of ethylacetate and the organic layer was washed with sat. NaHCO$_3$(30 ml) and then with sat. brine(30 ml), dried over anhydrous MgSO$_4$, and the solvent was removed therefrom. The resulting crude product as recrystallized from acetone/hexane, to obtain 3.99 g of the title compound as a white-light brown solid (yield: 90%).

m.p.: 164–165° C. (decomposition)

Mass: m/z=392.1(M+Na)$^+$, 370.05(M+1)$^+$, 354.1, 252, 119.0

1H-NMR(300 MHz,CDCl$_3$) δ (ppm): 2.20(s,3H), 4.33–4.41(q,2H), 4.73–4.88(q,2H), 6.66–6.68(d,1H), 7.26–7.30(m,2H), 7.51–7.71(m,2H), 8.34–8.36(d,1H)

Comparative Example 1

The procedure of Example 2 was repeated except that the free radical catalyst was not used. The crude product was purified by silica gel column chromatography and recrystallization, to obtain 2.79 g of lansoprazole as a white-light brown solid (yield: 63%).

Comparative Example 2

2.23 g of 2-[3-methyl-4-(2,2,2-trifluoroethoxy)-2-pyridyl]methylthio-1H-benzimidazole(6 mmol) prepared in Example 1 was dissolved in 20 ml of chloroform, 1.24 g of m-chloroperbenzoic acid(1.2 equivalent) dissolved in 20 ml of chloroformwas added thereto dropwise at below 5° C., and stirred at the same temperature for about 10 minutes. The reaction mixture was washed with aqueous NaHCO$_3$ and dried over MgSO$_4$. The residue obtained after removing the solvent under a reduced pressure was purified by silica gel column chromatography and recrystallization, to obtain 1.33 g of lansoprazole as a white-light brown solid (yield: 60%).

Comparison of Formation Rate of Impurities

Lansoprazole products obtained in Example 2 and Comparative Examples 1 and 2 were each analyzed with HPLC (high performance liquid chromatography) and the result is shown in Table 1:

<Measurement Conditions of HPLC> column: Capcell pak C$_{18}$ (150×4.6 mm inner dia.)

wavelength: 254 nm transfer phase: 40% of acetonitrile having 0.1 mol of KH$_2$PO$_4$

TABLE 1

| | RT (min) | Area rate from HPLC (%) | | |
| --- | --- | --- | --- | --- |
| | | Example 1 | Com. Example 1 | Com. Example 2 |
| lansoprazole | 2.839 | 98.0973 | 92.1528 | 85.6436 |
| Byproduct of formula (VI) | 3.595 | 0.0834 | 3.0078 | 9.5431 |
| Compound of formula (II) | 5.842 | 1.8193 | 4.8394 | 5.4133 |
| Yield | | 90% | 83% | 80% |

As the result in Table 1 shows, both lower yields of lansoprazole and higher levels of impurities represented by the compound of formula (VI) were obtained in Comparative Examples 1 and 2 as compared with Example 1 which was conducted according to the present invention.

While the invention has been described with respect to the specific embodiments, it should be recognized that various modifications and changes may be made by those skilled in the art to the invention which also fall within the scope of the invention as defined as the appended claims.

What is claimed is:

1. A method for preparing lansoprazol of formula (I) comprising (a) reacting the compound of formula (III) with the compound of formula (V) in the presence of a phosphine compound and a dialkyl azodicarboxylate to form the compound of formula (II); and (b) reacting the compound of formula (II) with an oxidant in a mixture of water and an organic solvent in the presence of both an organic free radical and a phase transfer catalyst:

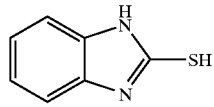

(I)

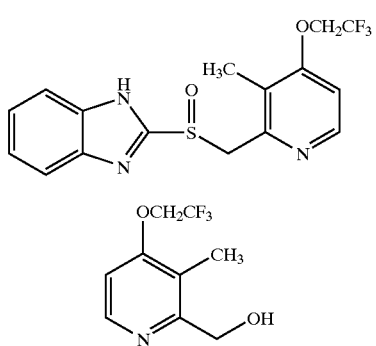

(III)

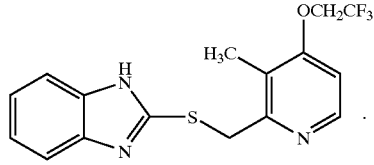

(V)

(II)

2. The method of claim 1 wherein step (a) is carried out at 0° C. to room temperature for 1 to 2 hours.

3. The method of claim 1 wherein the phosphine compound is selected from the group consisting of triethyl phosphine, trimethyl phosphine, tributyl phosphine, triphenyl phosphine and a mixture thereof.

4. The method of claim 1 wherein the alkyl azodicarboxylate is diisopropyl azodicarboxylate or diethyl azodicarboxylate(DEAD).

5. The method of claim 1 wherein the organic radical catalyst is selected from the group consisting of diphenyl nitrosyl radical, di-tert-alkyl nitrosyl radical, 2,2,6,6-tetramethyl-1-piperidinyloxy(TEMPO) free radical, 4-methoxy-TEMPO free radical and a mixture thereof.

6. The method of claim 1 wherein the oxidant is sodium hypochlorite used in a 1 to 3 equimolar amount based on the amount of the compound of formula (II).

7. The method of claim 1 wherein the phase transfer catalyst is selected from the group consisting of tetrabutyl ammonium fluoride, tetrabutyl ammonium chloride, tetrabutyl ammonium bromide, tetrabutyl ammonium iodide and a mixture thereof.

* * * * *